US010359348B1

(12) United States Patent
Lytle

(10) Patent No.: US 10,359,348 B1
(45) Date of Patent: Jul. 23, 2019

(54) HELMET IMPACT SIMULATOR AND METHOD

(71) Applicant: Protective Sports Equipment International Inc, West Chester, PA (US)

(72) Inventor: Frank Lytle, West Chester, PA (US)

(73) Assignee: Protective Sports Equipment International, Inc., Chester Springs, PA (US)

( * ) Notice: Subject to any disclaimer, the term of this patent is extended or adjusted under 35 U.S.C. 154(b) by 0 days.

(21) Appl. No.: 15/376,914

(22) Filed: Dec. 13, 2016

(51) Int. Cl.
| | | |
|---|---|---|
| G01M 7/08 | (2006.01) |
| G01N 3/30 | (2006.01) |
| G01N 3/303 | (2006.01) |
| G09B 23/30 | (2006.01) |
| G09B 23/32 | (2006.01) |
| G09B 9/00 | (2006.01) |
| G09B 5/02 | (2006.01) |
| G01N 23/04 | (2018.01) |
| G01P 15/00 | (2006.01) |
| G01L 5/00 | (2006.01) |
| F41H 1/04 | (2006.01) |
| G01N 33/00 | (2006.01) |

(52) U.S. Cl.
CPC .............. *G01N 3/30* (2013.01); *G01L 5/0052* (2013.01); *G01M 7/08* (2013.01); *G01N 23/04* (2013.01); *G01P 15/00* (2013.01); *G09B 5/02* (2013.01); *G09B 9/00* (2013.01); *G09B 23/32* (2013.01); *F41H 1/04* (2013.01); *G01N 2033/008* (2013.01)

(58) Field of Classification Search
CPC ...................................................... G01N 23/04
See application file for complete search history.

(56) References Cited

U.S. PATENT DOCUMENTS

| 7,204,165 B1* | 4/2007 | Plaga ................ G01M 17/0078 73/12.01 |
| 2012/0247178 A1* | 10/2012 | Kis, Jr. .................... G01N 3/30 73/12.04 |

(Continued)

OTHER PUBLICATIONS

Hardy, Warren N., et al. "A study of the response of the human cadaver head to impact." Stapp car crash journal 51 (2007): 17.*

*Primary Examiner* — Son T Le
*Assistant Examiner* — Herbert K Roberts
(74) *Attorney, Agent, or Firm* — Invention To Patent Services; Alex Hobson

(57) ABSTRACT

A head impact test apparatus is configured to enable viewing a head model including a brain component that may be at least partially surrounded by a fluid component and within a skull component. A head model may be a cross-sectional model of a person's head and have a translucent cover extending over the cross-sectional plane to enable viewing and image capture of the components of the head model. A camera may be configured to take a plurality of images during an impact test. These images may be analyzed to determine the acceleration and deformation of the brain component. An impact element is configured to impact the head model and the head model may have any type of helmet thereon. A helmet component may comprise a helmet cover. The test may be used to determine the effectiveness of helmets and helmet covers in reducing brain trauma.

15 Claims, 17 Drawing Sheets

(56) References Cited

U.S. PATENT DOCUMENTS

2014/0060202 A1* 3/2014 Carbo, Jr. ............... G01M 7/08
                                                    73/855
2015/0289911 A1* 10/2015 Beyar ................ A61B 17/7059
                                                    606/70
2016/0220206 A1* 8/2016 Petel ................... A61B 5/1128

* cited by examiner

HELMET IMPACT SIMULATOR AND METHOD

CROSS-REFERENCE TO RELATED APPLICATIONS

This application is a divisional application of U.S. patent application Ser. No. 15/067,846, filed on Mar. 11, 2016 and currently pending, which claims the benefit of priority to U.S. provisional patent application No. 62/132,504, filed on Mar. 13, 2015 and entitled Helmet Impact Simulator Test and Method; the entirety of both are incorporated by reference herein.

BACKGROUND OF THE INVENTION

Field of the Invention

The present invention relates to a test apparatus for measuring the effect of a head impact on the brain, the corresponding effectiveness of helmets on reducing these effects and tests methods employing said test apparatus.

Background

Chronic traumatic encephalopathy (CTE) is a progressive degenerative disease resulting from a head trauma and particularly a history of repetitive head trauma. Military personnel may be exposed to blasts and other head impacts which may lead to development of CTE. Other environments where people may be subjected to head trauma is the health care industry, industrial environments, such as in a factory or construction site, and commercial industries. Athletes participating in contact sports such as football, soccer, rugby and boxing incur repetitive head trauma that has been shown to lead to the development of CTE in some individuals. CTE may result from symptomatic concussions as well as sub-concussive head trauma. Many athletes may experience frequency sub-concussive head trauma during participation in a contact sport and never have a symptomatic concussion. These athletes may still develop CTE however and the effects of these frequent head impacts is a growing concern.

CTE may result from repetitive damage to axons in the brain, such as shearing caused by high acceleration of the brain tissue. High acceleration is caused by rapid head velocity change, such as that caused by an impact to the head. Axons connect neurons in the brain. Damage to the axons can result in immediate effects and/or delayed effects, such as CTE. Brain injury, such as axonal shearing, may create neurochemical and neurometabolic cascade effects. Even mild trauma to the brain can result in neuronal depolarization which leads to neuronal discharge and the release of neurotransmitters and increased extra cellular potassium ($K^+$). This may be followed by an increased glucose demand and metabolism (hyperglycolysis) and a resultant relative ischemia from reduced cerebral blood flow. Axonal injury may also result from an influx of extra cellular calcium that reduces cerebral blood flow through vasoconstriction, and the release of oxygen free radicals. These neurochemical and neurometabolic effects from even mild head trauma, may result in the development of CTE.

There are a wide number of test methods that measure the forces and acceleration effects and benefits of wearing a helmet, however none of these methods employ a simulated head model including a brain component. There is a need to measure the direct effects of head impact on the brain in an effort to develop helmets and protective head gear that will reduce brain acceleration and trauma.

SUMMARY OF THE INVENTION

The invention is directed to a helmet impact simulator and a method of use. The helmet impact simulator comprises a head model and an impact element configured to impact the head model. The impact test may be conducted with or without a helmet component configured over the head model. In an exemplary embodiment, a head model is configured with a translucent cover on the imaging side of the head model to enable a camera to take a plurality of images of the head model as it is impacted. The plurality of images may be analyzed to determine a motion factor, such as velocity, displacement, acceleration, deceleration of the brain component and/or deformation of the brain component, or portion of the brain and predict a level of brain trauma. The helmet impact simulator may be used to determine the effectiveness of various helmets, with or without helmet covers, to prevent brain trauma.

A head model may be a complete head model having a translucent skull and/or fluid component to enable viewing of the brain component therethrough. In another exemplary embodiment, a head model is a cross-sectional model of a person's head. A cross-sectional head model may be a cross-section from the front to the back of the head and thereby be a model of the left or right side of a head. In another embodiment, a head model is a cross-sectional from left to right and thereby be a model of the front or back portion of a head. In still another embodiment, a cross-sectional head model is through a plane that shows a top-down view of the head. Any suitable cross-section portion of a head may be used, including a cross-section of the top or bottom portion of a head.

An exemplary head model comprises a head exterior component, an interior cavity, a skull component, a brain component, a fluid component, an interior cavity surface and a translucent cover. The head model may comprise real anatomical components or components configured to simulate the real anatomy. For example, the brain component may be made out of a material that has a similar density and elasticity as a real brain including, but not limited to, an elastomer, such as silicone or urethane, and may be a foam material, polymeric materials including any suitable plastic, gel material, composite material and the like. Similarly, the fluid component may comprise a fluid that has similar viscosity to cerebrospinal fluid and in some embodiments, the fluid component is translucent or transparent to enable digital images to be taken of the brain component through the fluid component. The brain component is configured within the interior cavity of the skull component and is adjacent to a translucent cover on an imaging side of the head model. A transparent cover may be a transparent panel that extends across and is attached to the skull component. A dura component, such as a liner around a portion of the brain component, or around the perimeter of the brain component, may simulate an actual human dura and may be recognized by imaging analysis to determine the surface area and/or perimeter of the brain component. It is well known that image analysis software can detect an outline or shape of an element within the frame of a digital image and the dura component may be a color or shade that enables it to be more easily identified by the image analysis software. In one embodiment, the dura component is translucent over an imaging plane and a color or shade around the perimeter of the brain component, thereby enabling viewing of the brain component through the clear dura component portion and identification of the shaded dura component portion around the perimeter of the brain component. In another embodiment, a brain component comprises an outline pattern that enables imaging analysis to determine the surface area and any deformation of the brain component. In an exemplary embodiment, a pattern such a grid is configured on the brain component to further enable more detailed analysis of the deformation.

The head model may be coupled to a mount to restrain and provide stability during an impact test. A neck spring may couple the head model to a mount and may be flexible to enable some deflection and movement of the head model during an impact test. A neck spring may be made out of a deformable material that can be physically returned to an original orientation. In another embodiment, a neck spring is elastic and will return to substantially to an original orientation automatically after removal of a load or after an impact to the head model. A neck spring may comprise one or more springs. The impact element may be configured to impact the head model and then quickly retract, thereby allowing the head model to spring back or recoil from the impact. This simulates real world impacts or accelerations, such as a rear-end car accident.

The helmet impact simulator comprises a helmet component that is configured to fit over the head model. Any type of helmet or head cover may be used including, but not limited to, football, ice hockey, baseball, lacrosse, boxing, rugby, skiing, bicycling, military, health care, industrial, commercial and the like. The helmet component may comprise a transparent portion to enable viewing of the head model during an impact test. In another embodiment, a helmet component is a portion of a helmet, such as a helmet cut along the length to produce substantially two equal sides, left and right. A head model and helmet cover may be configured to simulate any portion of a person's head and may simulate one side of a person's head as described, a front portion of a person's head, a back portion of a person's head and the like. A simulated front portion of a person's head may be used to evaluate side impacts and a side simulate portion of a person's head may be used to evaluate front and back impacts.

A helmet configured on the head model may comprise a helmet cover. Any suitable helmet cover may be evaluated with the head impact simulator test, as described herein. A helmet cover may comprise an impact absorbing material that may be elastomeric and a skin, or cover layer over the impact absorbing material. A helmet cover may comprise a cellular or foam material that may be reusable or disposable. A helmet cover may comprise a helmet cover described in U.S. Pat. No. 7,328,462 to Albert E. Straus, and U.S. Pat. No. 8,776,272 to Frank Lytle et al. Any suitable combination of helmet and helmet cover may be configured on a head model, as described herein.

An impact element may be configured to simulate any number of different types of impact surfaces and orientations. For example, an impact element may comprise or simulate concrete, the ground, metal, a bat, a ball, a vehicle, a person's head, or another helmet. The impact element may be coupled to an actuator that may be controlled in rate of displacement and acceleration. The actuator may be controlled to move the impact element at any suitable velocity and/or acceleration throughout the stroke or travel distance of the impact element. As described herein, the impact element may be controlled to retract back quickly after impacting with the head model or helmet component. A helmet impact simulator may comprise one, two or more impact elements configured to impact the head model at substantially the same time, or in rapid succession, for example. In an exemplary embodiment, an impact element is a helmet impact element comprising a helmet or portion of a helmet and, in some embodiments, a helmet cover.

In an exemplary embodiment, a helmet impact simulator comprises a camera that is configured to take a plurality of images of the head model including the brain component through a translucent cover, translucent helmet of helmet cover and translucent head component. The camera may be a high speed camera to capture details of the displacement and deformation of the brain component. The plurality of images taken by the camera may be analyzed by a computer having a computer program that is configured for analyzing images or image analysis software. The computer program may determine, through image analysis, the acceleration of the brain component, deformation of the brain component and predict brain trauma. An exemplary image analysis program or software may be configured to recognize an element within an image, such as a digital image including shape, perimeter, outline, point, grid, an element within a grid or intersection of grid elements or nodes and then determine location change, shape change, volume change, displacement, velocity acceleration or deceleration of said element by comparing an element from one image to another image. In some cases, the image analysis software may take into account the time differential between a first and second image to determine rate of change effects including velocity, acceleration or deceleration.

In one embodiment, the brain component comprises an outline that may be recognized by the image analysis software. In an exemplary embodiment, a brain component comprises a pattern around the perimeter or across an imaging plane and the computer program detects pattern in the plurality of images and calculates the surface area of the brain component as a function of time. The rate of change of surface area may correlate with deformation, and/or compression, of the brain component. In another embodiment, a brain component comprises a grid pattern and the computer program detects the grid pattern as well as changes in the grid pattern as a function of time. The changes in discrete grids, or cells, in the pattern may correlate with acceleration and/or deformation of the brain component. An imaging analysis software may be programmed to recognize a grid pattern, grid elements, or connections or intersections of grid elements. A grid element is an elongated line used to form said grid and grid elements may be configured at offset angles, such as perpendicular to each other to form a grid having a plurality of squares cells formed thereby. Finite element analysis may be employed in conjunction with a pattern, particularly a grid pattern, to determine forces exerted on the brain component. In another embodiment, the brain component comprises an outline pattern of two or more brain portions. A brain portion of a brain component may include a frontal lobe, parietal lobe, occipital lobe, cerebellum and/or temporal lobe. An outline around or outline pattern around each of the brain portions may be recognized by the computer program and acceleration, forces, and/or deformation of each portion may be determined by image analysis. The brain portions may be different colors or have different patterns to further enable differentiation by the computer program.

In another embodiment, one or more radio-opaque materials, such as a metal and/or electrically conductive material is configured with the brain model as an imaging element. Radio-opaque materials may be configured in a brain model and may be imaged during an impact test by way of X-ray imaging, or ultrasound, for example. High speed X-ray video and imaging systems, such as that available form Teledyne DALSA, may be used to take high speed X-ray images, up to 30 frames per second, to determine the movement and deformation of a brain component having a radio-opaque image element. In an exemplary embodiment, the brain component has a radio-opaque perimeter or a radio-opaque dura component lining. The perimeter of the brain may be coated with a metallic material or comprise one or more metal wires around the perimeter. A radio-opaque perimeter of one of the head model components may be a metallic coating, such as a vapor deposited coating. It may be important to keep the radio-opaque imaging element supple, as to not influence the simulation by changing the mechanical properties of the components within the head model. Likewise, a metal component may be added to the fluid component. In an exemplary embodiment, a radio-opaque grid is configured within at least one plane of the brain component and the radio-opaque grid provides discrete cells or blocks define by the radio-opaque grid that can me captured by X-ray imaging. In an exemplary embodiment, a full head model comprises a radio-opaque grid pattern that is printed along a substantially centered and horizontal plane of the brain component and an X-ray imaging system is configured above the head model for capturing high speed X-ray video during an impact test. In another exemplary embodiment, a full head model comprises a radio-opaque grid pattern, comprised of metal threads or wires that may be configured to form a grid patter along a plane of the brain component and an X-ray imaging system is configured to one side of the head model for capturing high speed X-ray video during an impact test. In still another embodiment, a radio-opaque grid patter is configured in both a vertical and a horizontal plane and two X-ray imaging systems are configured above and to one side of the head model to capture X-ray video during an impact. This method may provide useful data for predicting head trauma and for determining the effectiveness of helmets and/or helmet covers without the need for a translucent cover or translucent portion, as described herein. Most helmets are made out of plastic materials that would not interfere with the X-ray video imaging.

Any number of other sensors for taking measurements of an impact event to the head model may be employed in the head impact test simulator, as described herein. For example, accelerometers and stress-strain gauges may be configured on the head model including any portion of the head model, such as the brain component, and/or the helmet or helmet cover, to take readings during an impact event. These readings, or measurements, may be taken as a function of time such that a correlation between a measurement and a visual motion factor is provided. For example, a deformation of the brain component may be correlated with a velocity and/or acceleration measurement taken by a sensor.

An exemplary helmet impact test apparatus may be used to conduct any number of tests to simulate an impact to a person's head, with or without a helmet configured thereon. An exemplary method of impact testing a helmet component comprises the steps of providing a helmet impact test apparatus as described herein; impacting the helmet component with an impact element; taking a plurality of images, i.e. digital photographs; and, analyzing the plurality of images to determine a motion factor of the brain component. A motion factor may be displacement, velocity, acceleration, deceleration, force, deformation and the like. As described herein, the impact test may be conducted with a helmet cover configured on the helmet component. In addition, an impact element may be a helmet impact element, with or without a helmet cover. The impact test may be utilized to compare the motion factors of a similar impact when different types of helmet components and/or helmet covers are evaluated.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
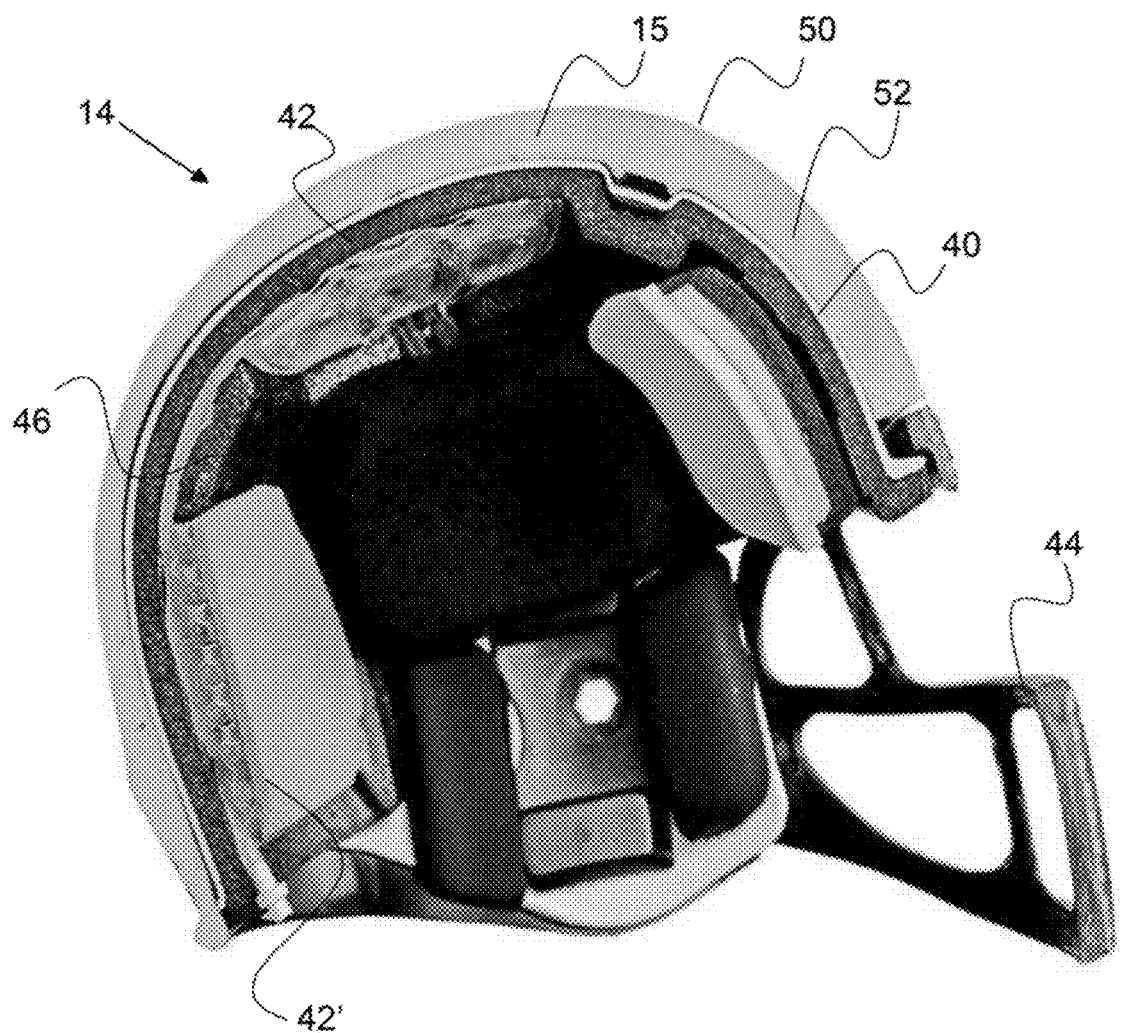

FIG. 1 shows a black-and-white photograph of a cross-section of an exemplary helmet having a helmet cover configured thereon.

Figure 2:
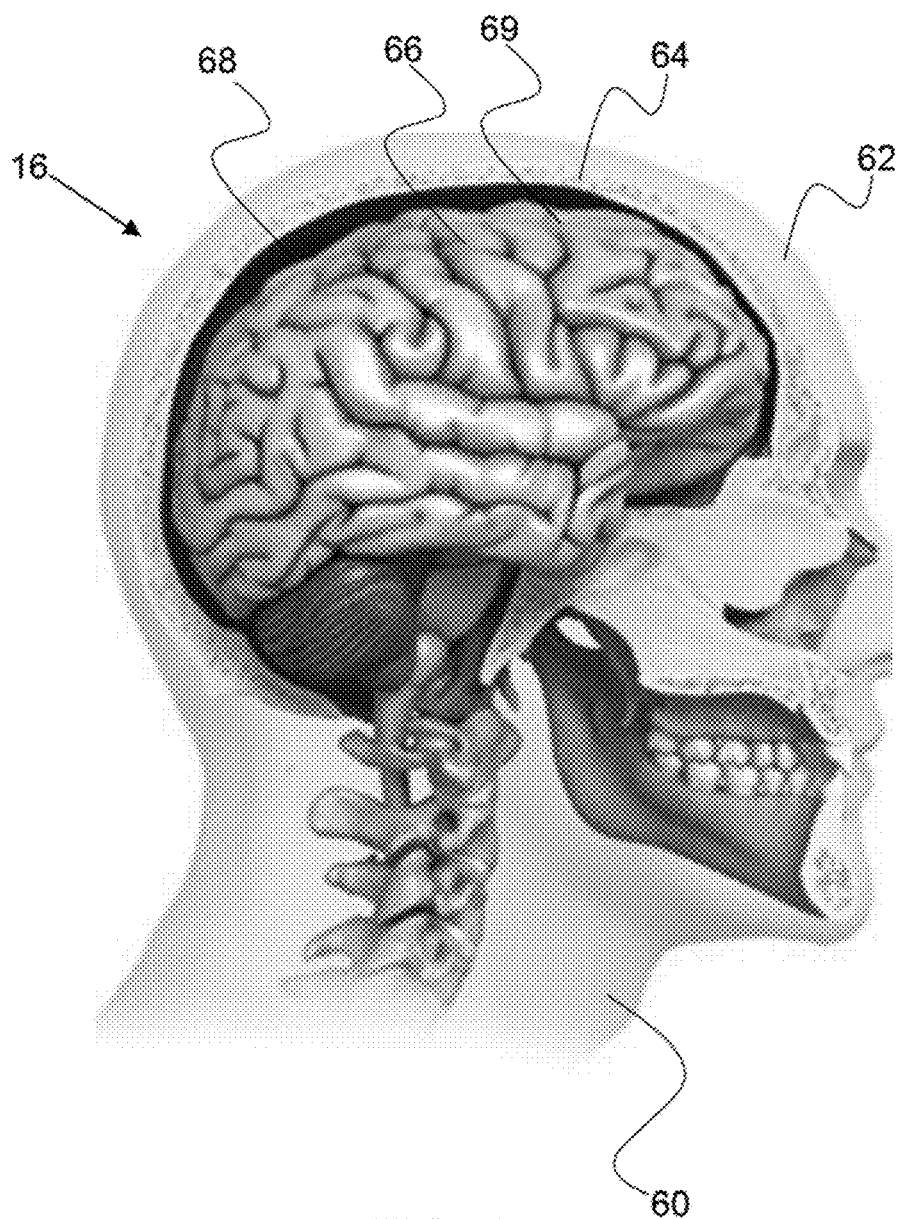

FIG. 2 shows a cross-section diagram of a person's head having the brain configured within the skull.

Figure 3:
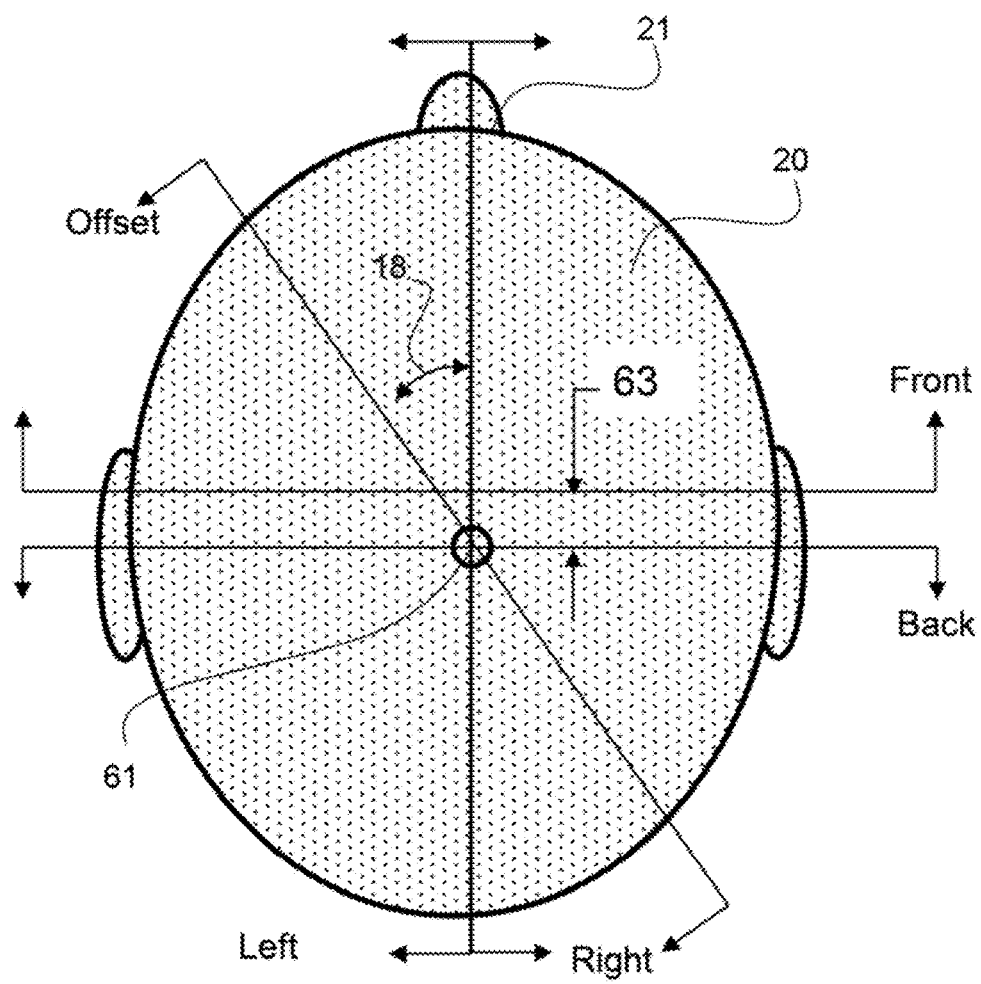

FIG. 3 shows a top-down view of a diagram of a head and cross-sectional planes that may be used in a head model.

Figure 4:
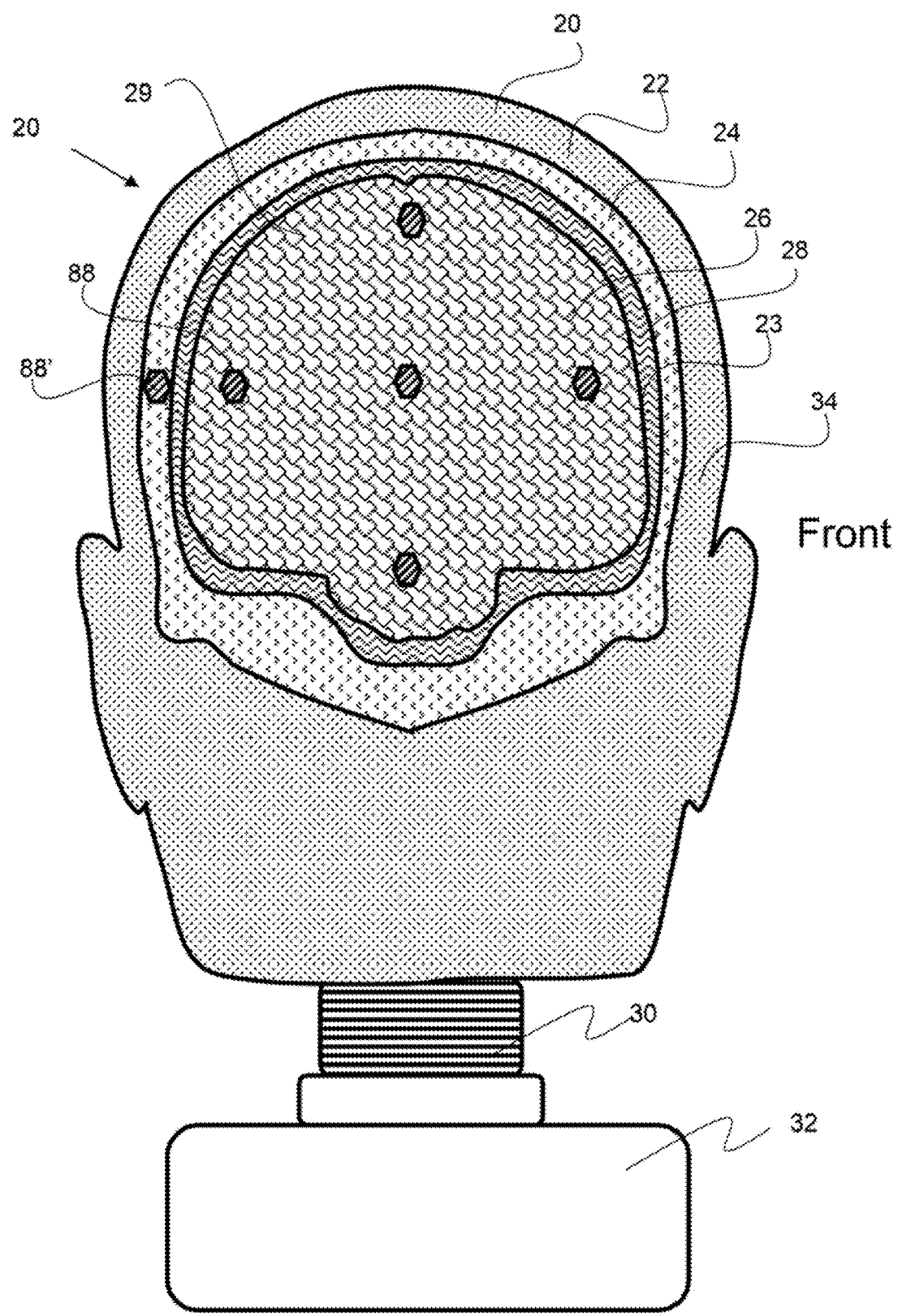
Figure 4:
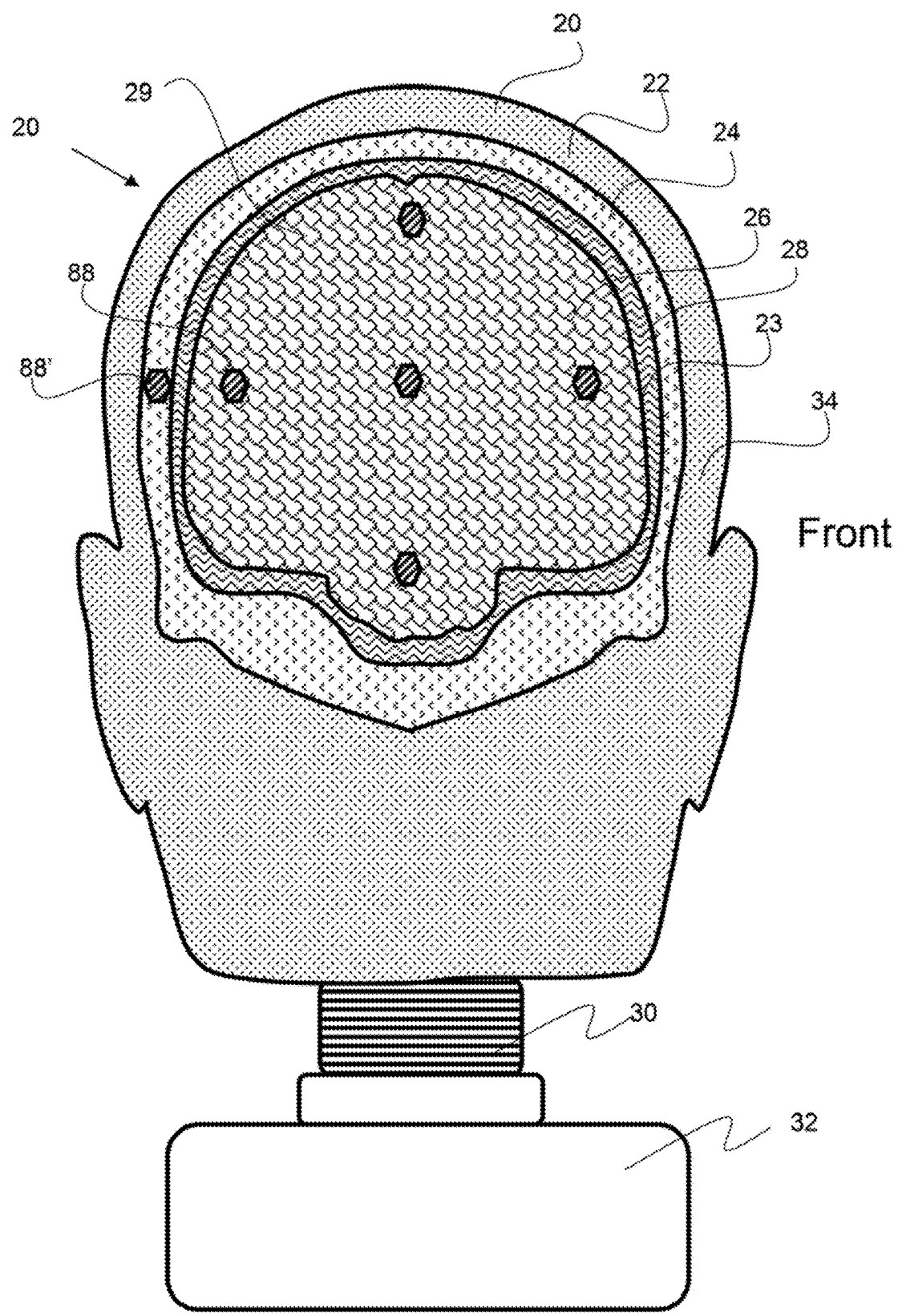

FIG. 4 shows an exemplary head model that is a cross-sectional front head model, or a head model of a front portion of a head, as shown in FIG. 3.

Figure 5A:
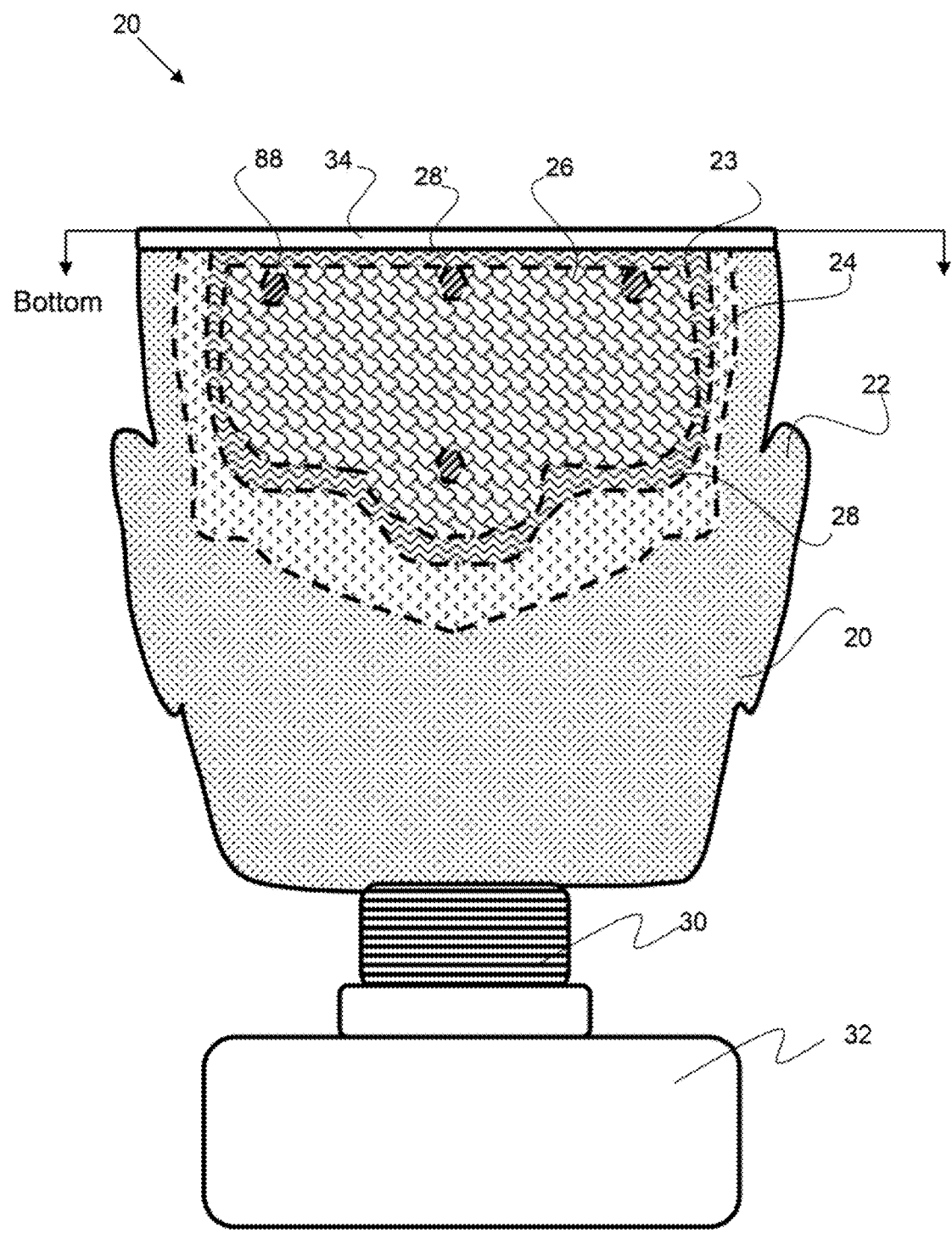

FIG. 5A is an exemplary head model that is a cross-sectional bottom head model, or a head model of a bottom portion of a head.

Figure 5B:
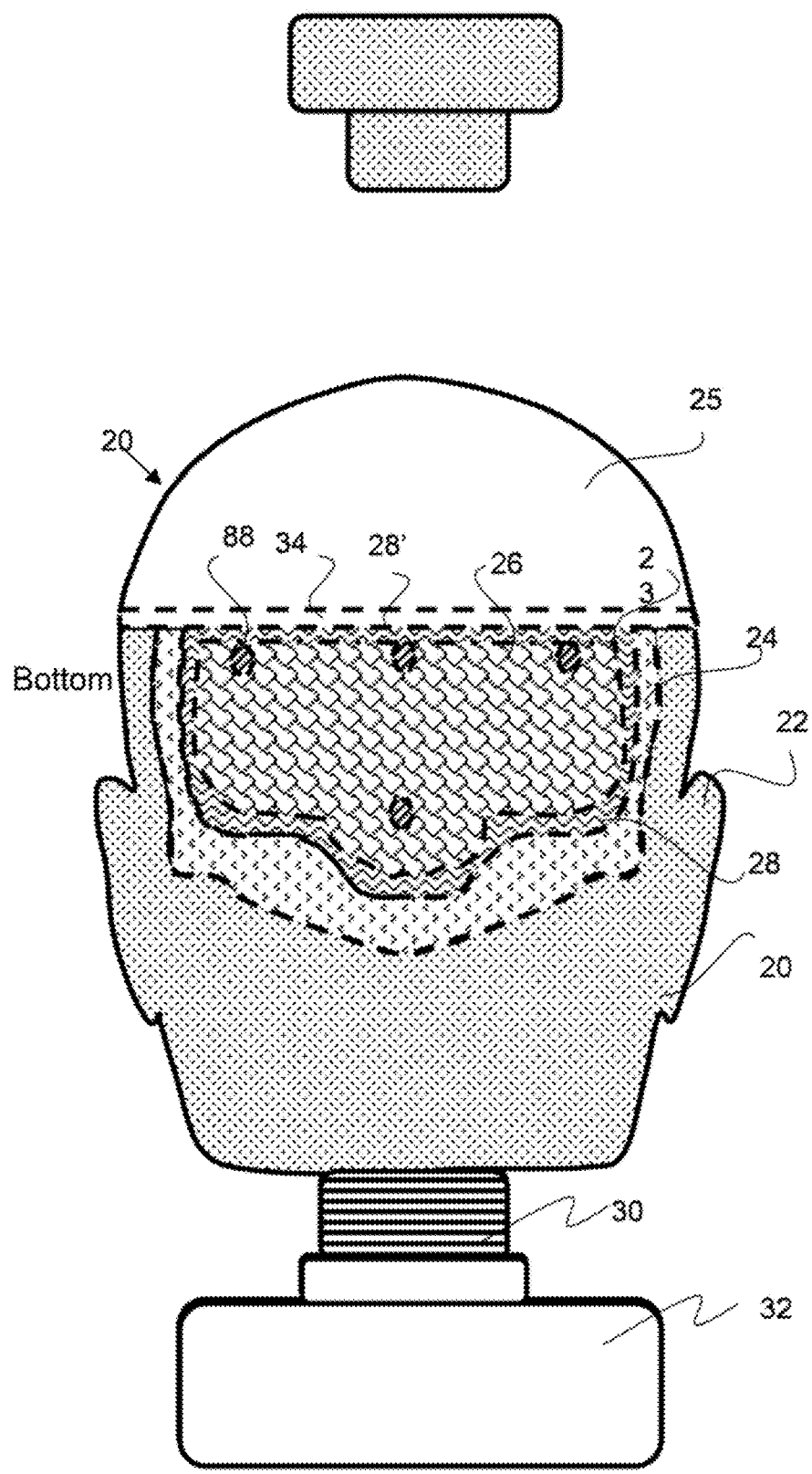

FIG. 5B is an exemplary full head model having a translucent portion configured at the top of the head model.

Figure 5C:
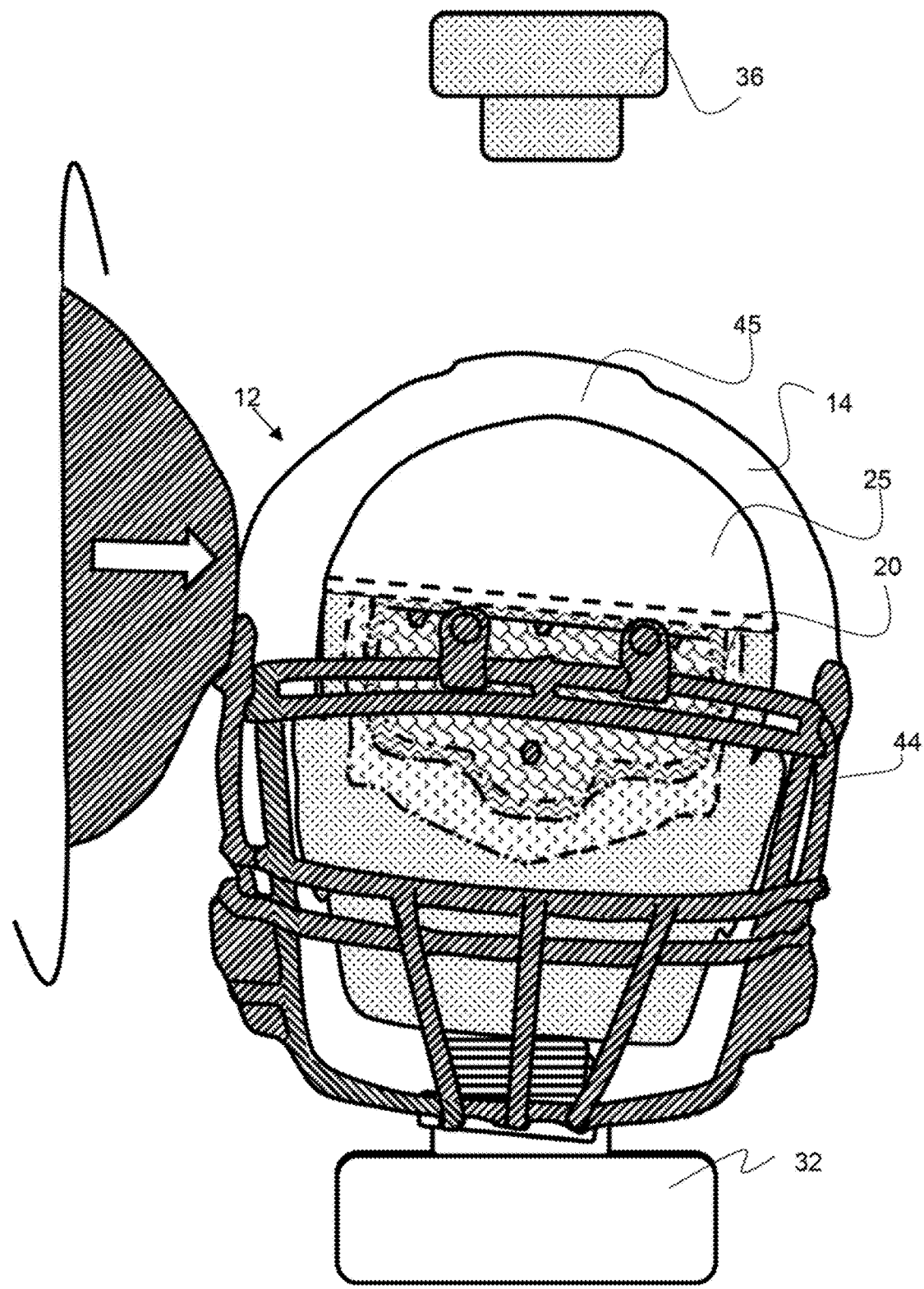

FIG. 5C is the exemplary head model shown in FIG. 5B with a full helmet configured thereon during an impact test.

Figure 6:
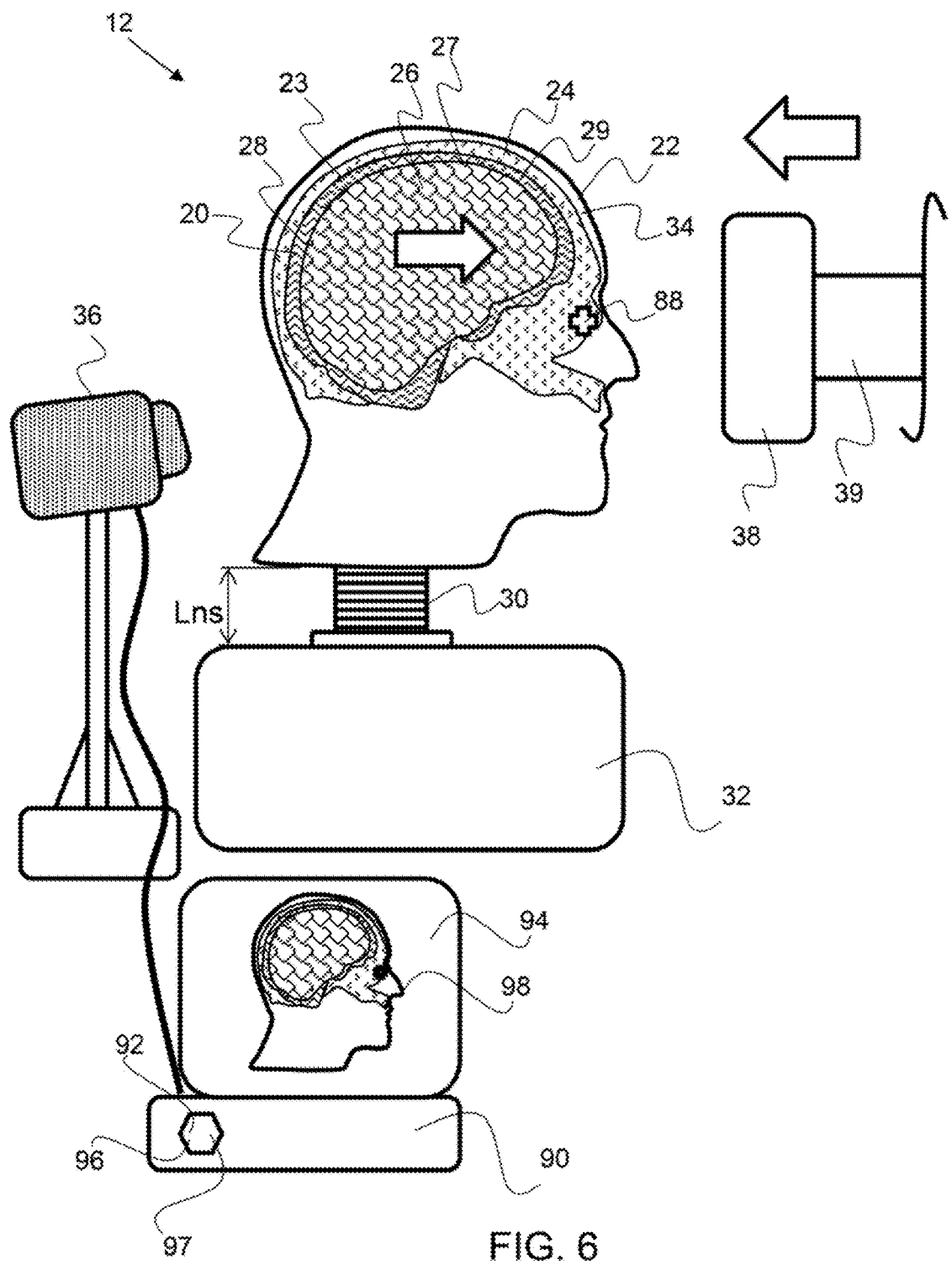

FIG. 6 shows an exemplary head impact simulator comprising a head model having a skull and brain component and an impact element configured to strike the head model.

Figure 7A:
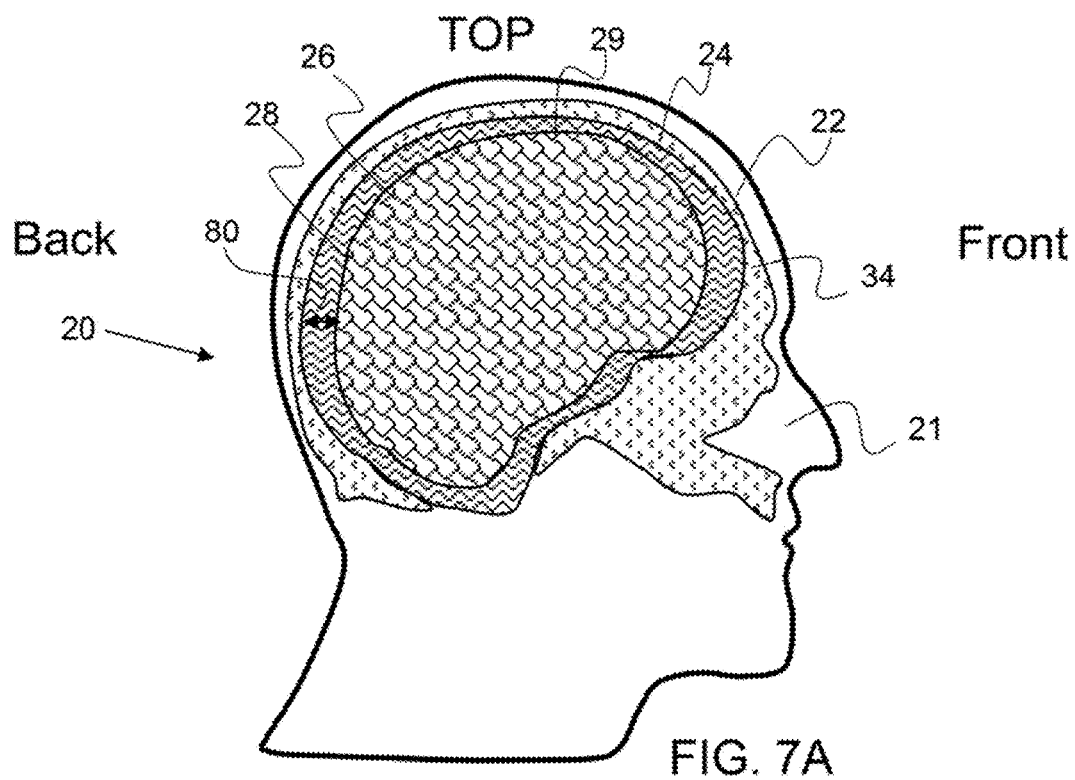

FIG. 7A shows an exemplary head model prior to an impact.

Figure 7B:
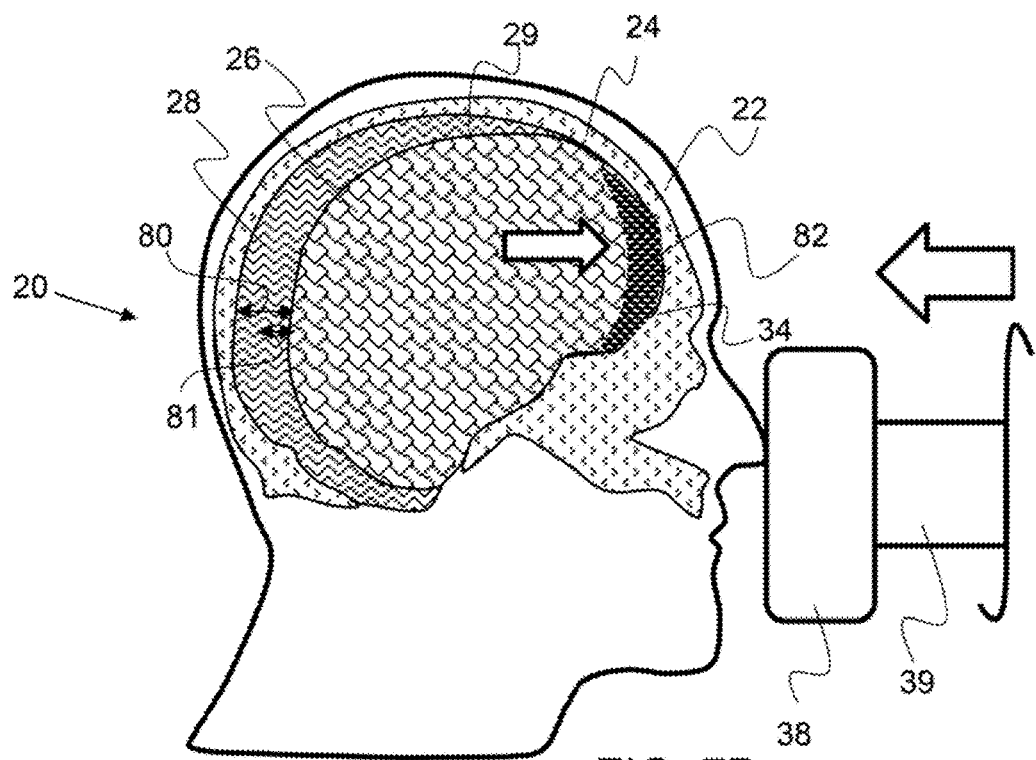

FIG. 7B shows the head model of FIG. 7A with the brain component impacting the interior of the skull component after an impact.

Figure 8:
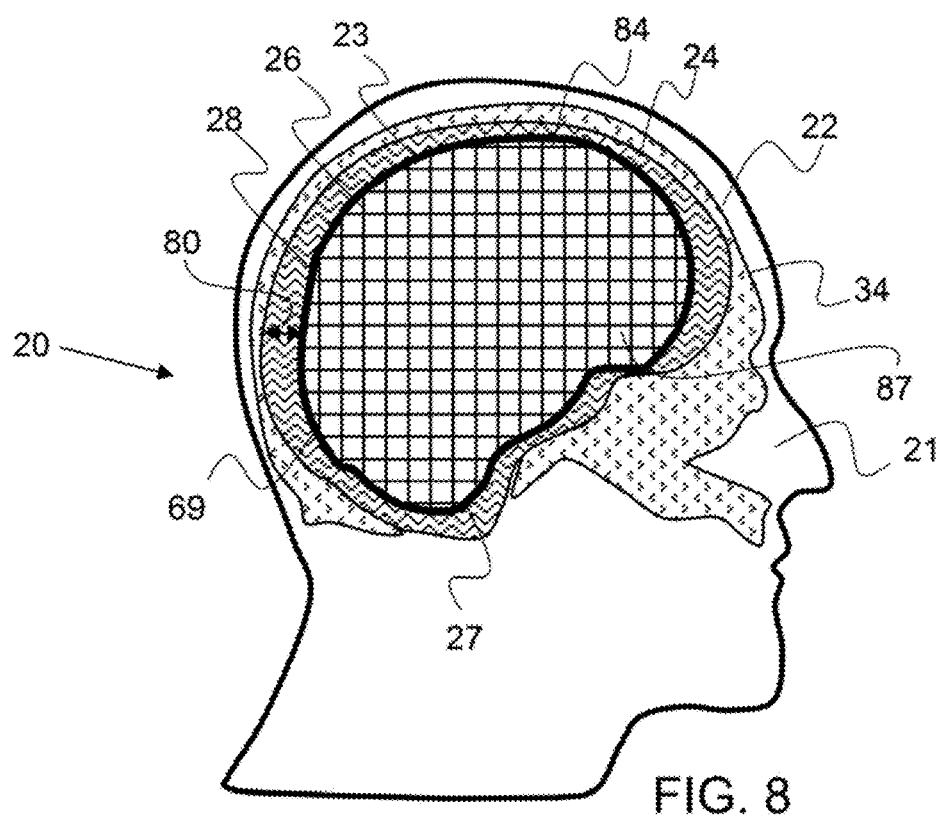

FIG. 8 shows an exemplary head model having a brain component having a grid pattern thereon.

Figure 9:
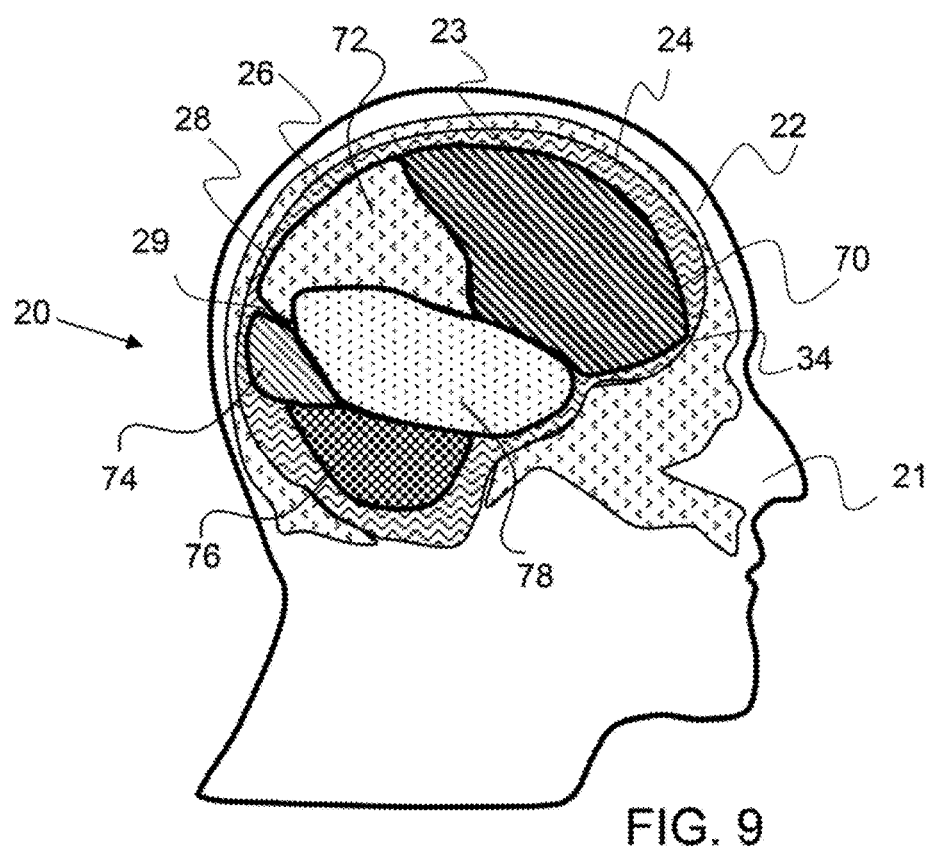

FIG. 9 shows an exemplary head model having a brain component with distinct brain portions.

Figure 10:
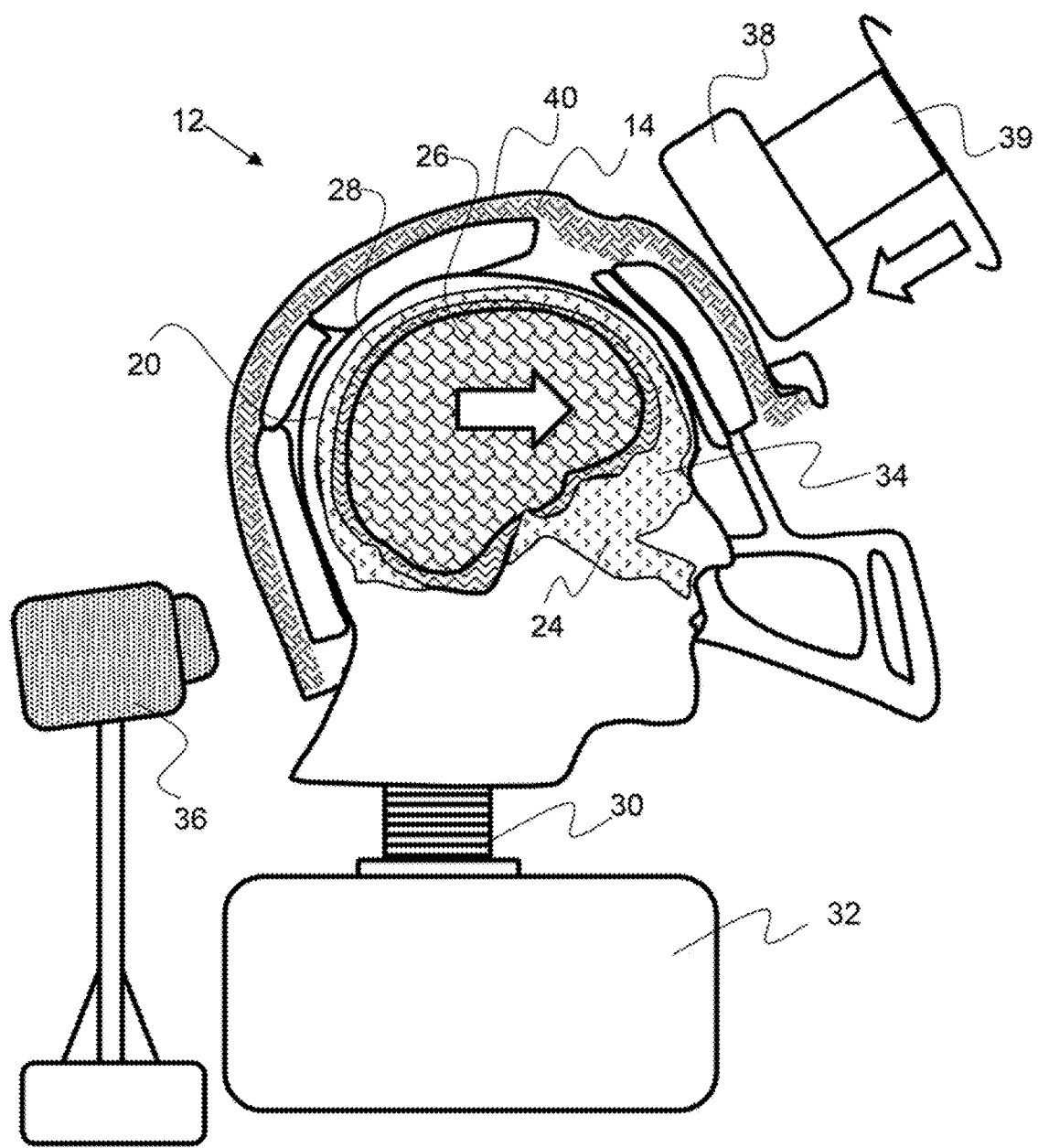

FIG. 10 shows an exemplary head impact simulator with an impact element impacting with a helmet component configured over the head model and a camera configured to take a plurality of images through a translucent cover.

Figure 11:
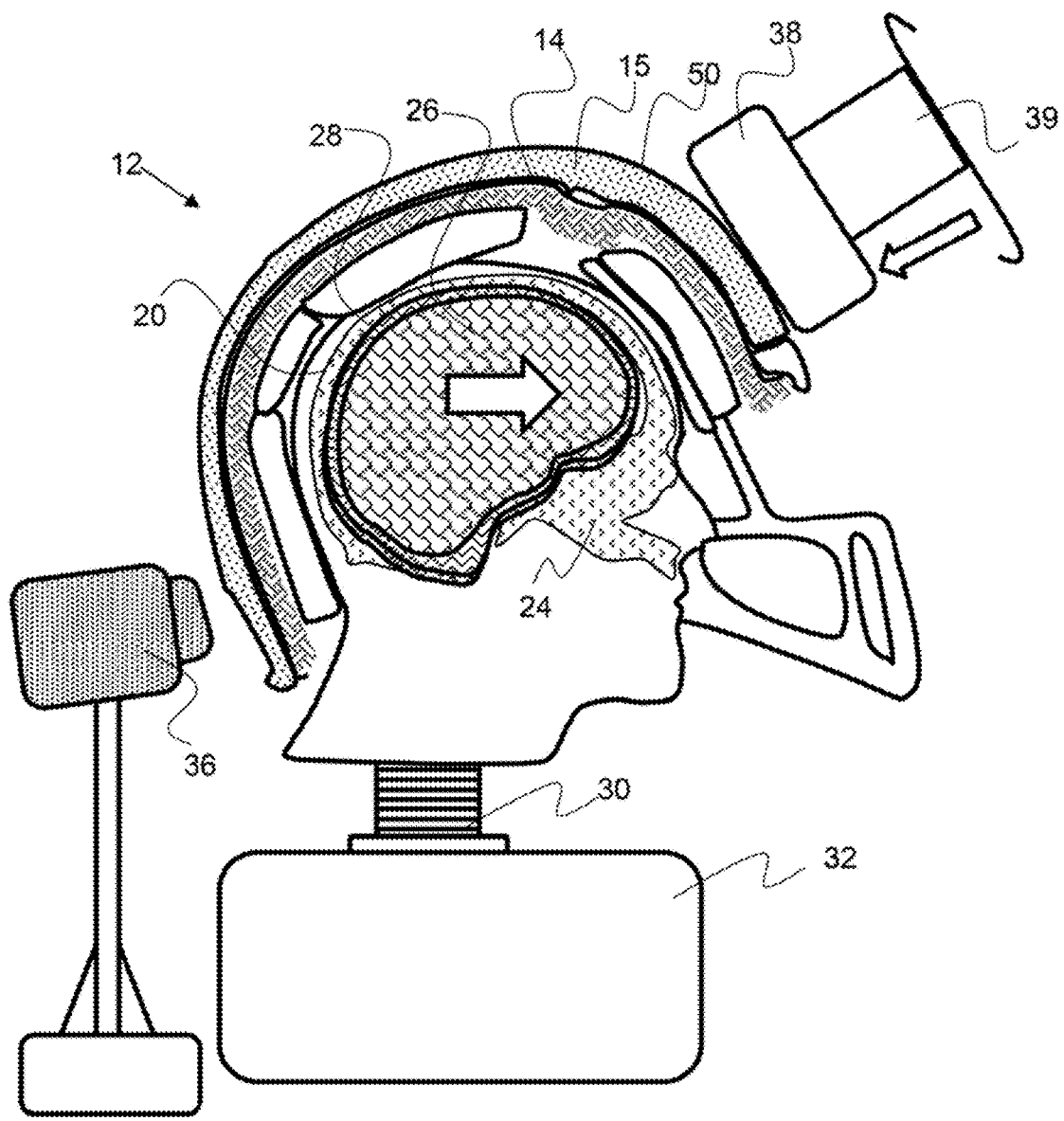

FIG. 11 shows an exemplary head impact simulator with an impact element impacting with a helmet component having a helmet cover and configured over the head model.

Figure 12:
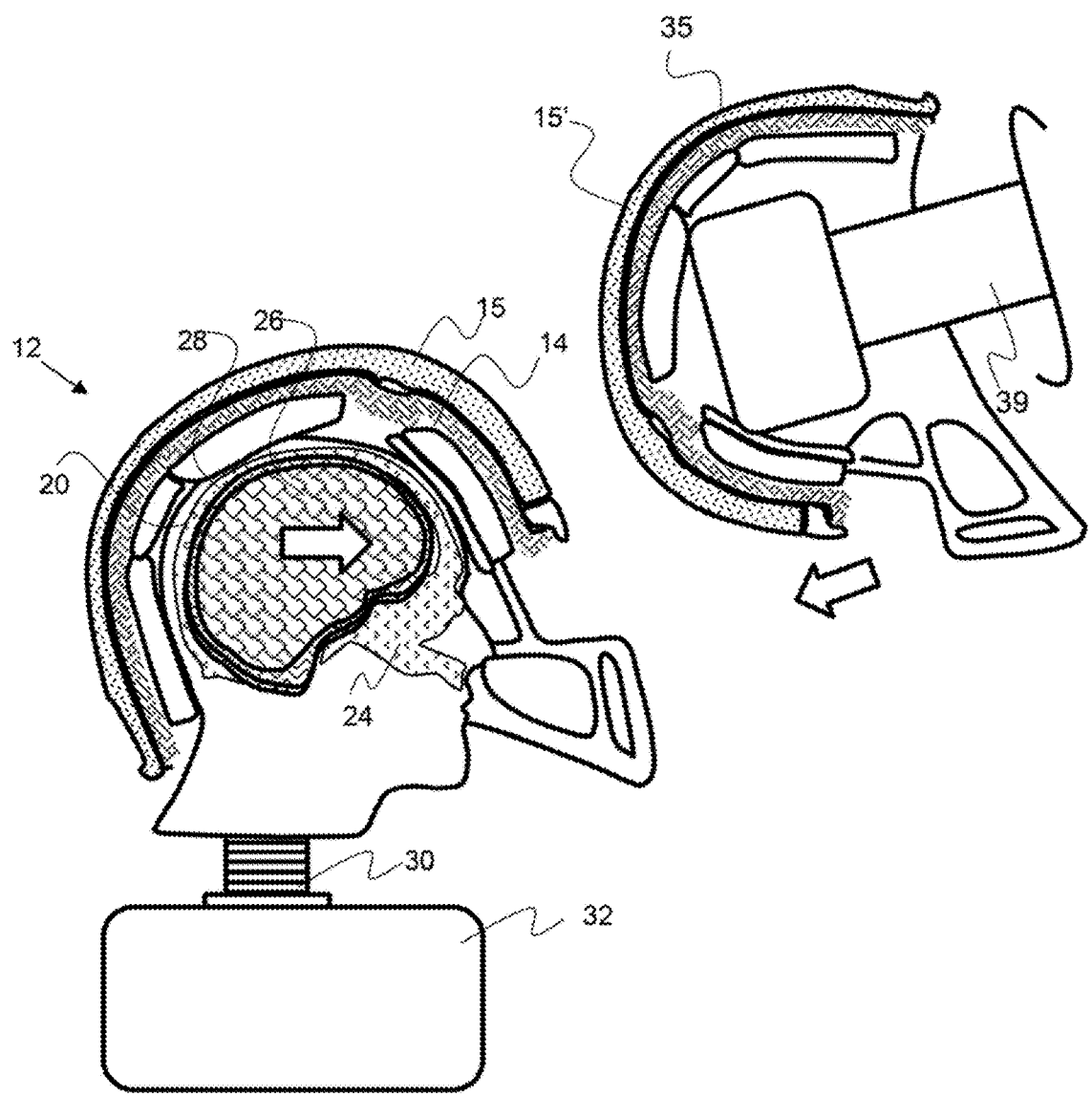

FIG. 12 shows an exemplary head impact simulator with a helmet impact element impacting with a helmet component having a helmet cover and configured over the head model.

Figure 13:
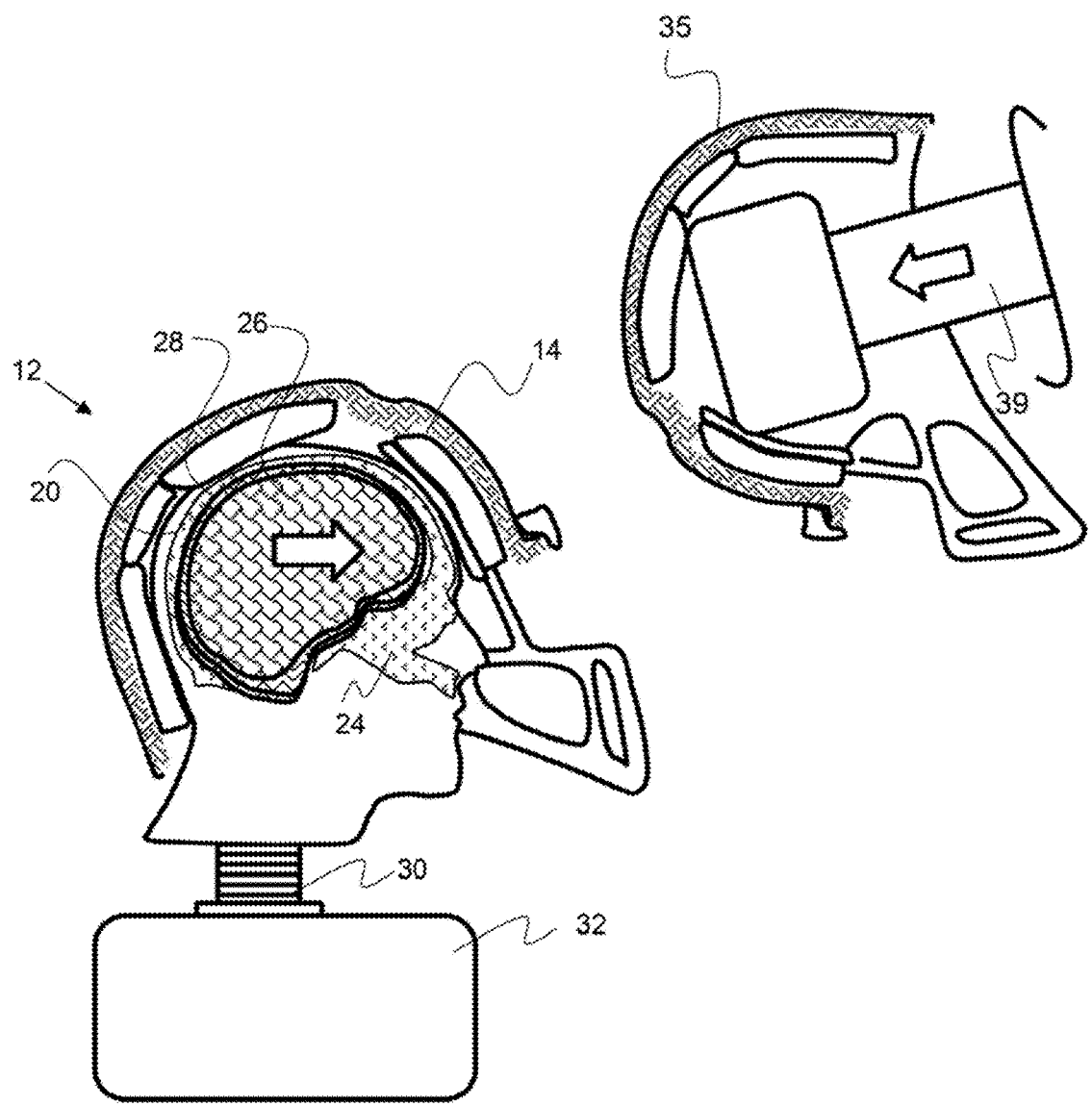

FIG. 13 shows an exemplary head impact simulator with a helmet impact element impacting with a helmet component configured over the head model; in this embodiment, neither the helmet impact element nor the helmet component have a helmet cover.

Figure 14:
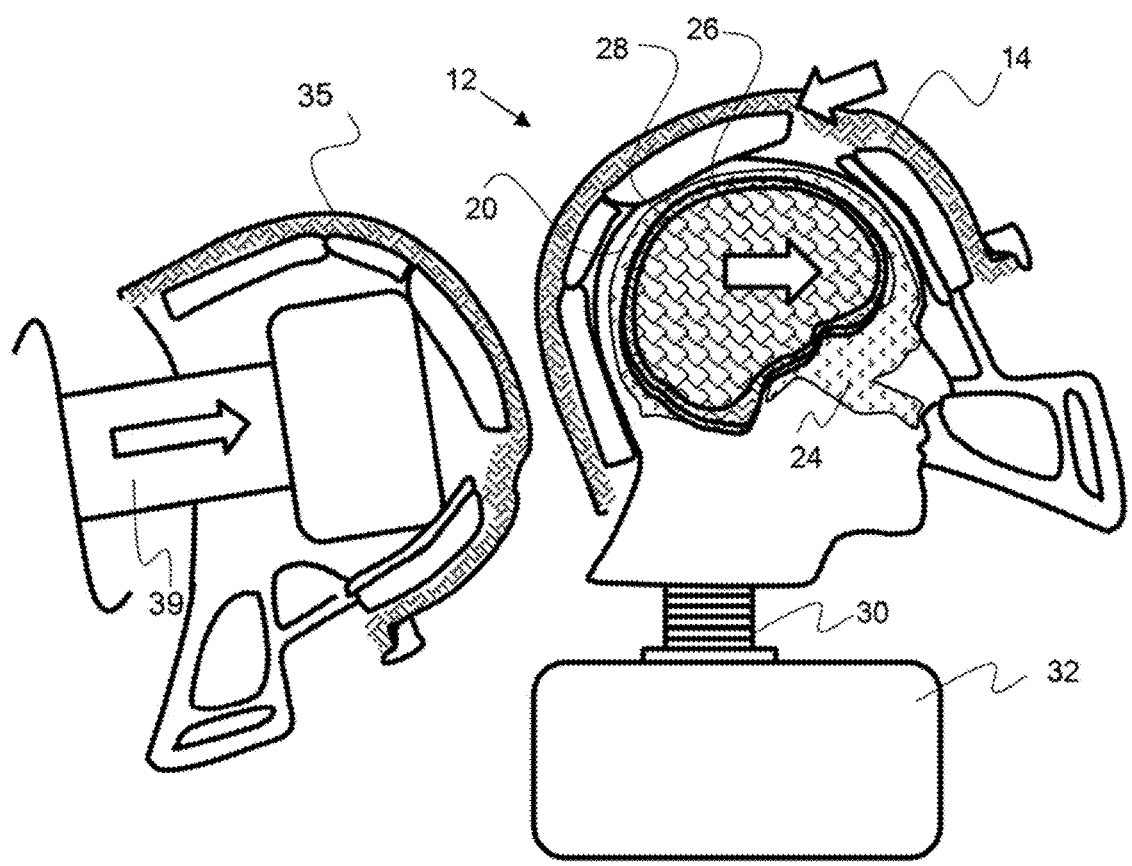

FIG. 14 shows an exemplary head impact simulator with a helmet impact element impacting with a helmet component on the back of the head model; in this embodiment, neither the helmet impact element nor the helmet component have a helmet cover.

Figure 15:
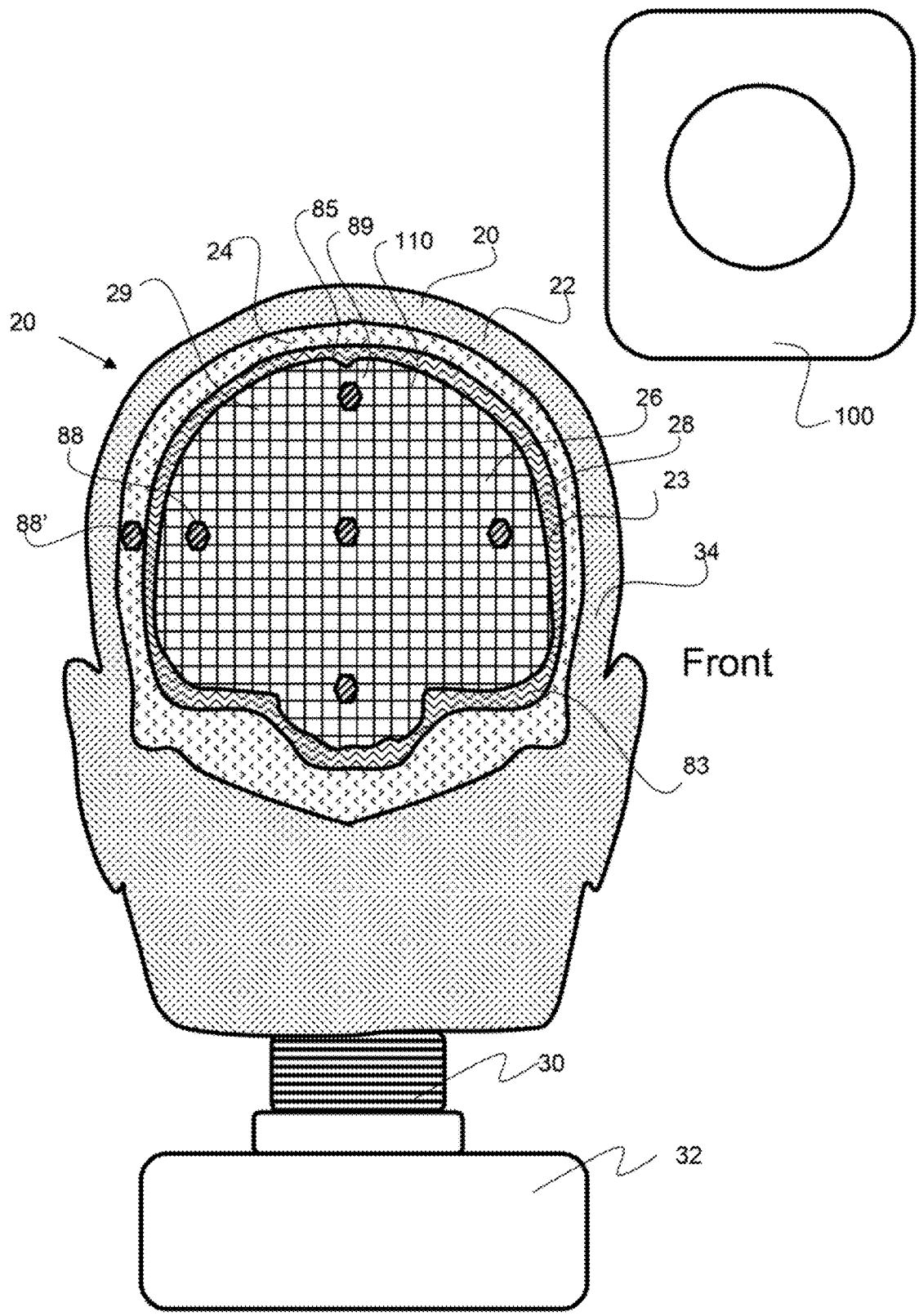

FIG. 15 shows a cross-section view of a full head model along the cross-sectional plane line "Front", as shown in FIG. 3, and having a radio-opaque grid configured along a vertical plane within the brain component.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary helmet component 14 comprises a helmet cover 15 configured thereon. The helmet component is a football helmet having an outer shell 50, impact absorbing material 42 configured within the outer shell and a face mask 44. The helmet cover 15 has an outer skin 50 and impact absorbing material 52 configured therein and an inner skin, or cover layer, to protect the interior impact absorbing material. The helmet component has an open side 46 along the cross-sectional plane of the helmet component. A helmet cover may be configured over a helmet to reduce the impact and resulting forces and acceleration on the brain. The helmet component used in the head impact simulator may be a helmet, with or without a helmet cover and may be provided with an open side along a cross-sectional plane, as shown. In another embodiment, a portion of a full helmet is made with translucent materials to enable viewing and image capture of the head model therein during an impact test.

As shown in FIG. 2, the brain 66 is configured within the skull 64 of a head 16. The cerebrospinal fluid 68 surrounds the brain and is configured between the brain and skull. A head model used in the head impact simulator may utilize materials that have similar physical attributes to a person's anatomy, including the dermal tissue, neck 60 and dura 69. Dermal tissue 62 is configured around the head 16.

As shown in FIG. 3, a head model 20 may be a cross-sectional head model taken along any suitable plane of a head 16. The cross-sectional planes shown in FIG. 3 may be an image plane, wherein the head model is viewed through a transparent cover along the cross-sectional image plane. The cross-sectional planes shown are vertical planes through the head. A cross-sectional plane may, however, be offset from a substantially vertical or horizontal plane. As shown in FIG. 3, a head model may be a Left or Right head model wherein the head model simulates about half of a head along a plane dividing the head from front to back. Likewise, a head model may be a Front or Back head model wherein the head model simulates about half of a head along a plane dividing the head from left to right. A head model may simulate about half of a person's head and extend substantially through a center point 61 of a head, or the head model may be offset an offset distance 63 from a plane extending through the center point. As shown in FIG. 3, a front cross-sectional plane is offset by offset distance 63 from a center point 61. In addition, a head model may be a model of a person's head taken along an offset angle to the front to back plane 18, as shown in FIG. 3.

In another embodiment, a head model is a full head model with components made out of a translucent material to enable viewing an image capture of the brain component. For example, a head model may be a full head model having a right side comprising a translucent head exterior component, a translucent skull component, or translucent portions thereof.

As shown in FIG. 4, an exemplary head model 20 is a cross-sectional front head model, or a head model of a front portion of a head, as shown in FIG. 3. The head model is coupled to a mount 32 by a neck spring 30. A translucent cover extends 34 over the cross-sectional plane of the head model. The translucent cover enables viewing and recording of movement of the various components of the head model within the interior cavity 29. The head model includes a brain component 26 that is configured within a skull-component 24 and at least partially surrounded by a fluid component 28. The fluid component may be translucent to enable viewing and image capture of the brain component therethrough. The head exterior component 22 extends around the perimeter of the skull component. A plurality of sensors 88 are configured on the various components of the head model. A number of sensors are configured in various locations of the brain component and sensor 88' is configured or attached to the skull component. A sensor may be a stress-strain sensor, or force sensor, or an accelerometer or any sensor to measure velocity, acceleration, force, or strain. With sensors attached to the brain component and the skull component, the difference in a motion factor, velocity or acceleration, or force may be determined. The skull component may be made out of a rigid material that will measure the general motion factors of the head model and the brain component may be more supple to simulate the reaction of a real brain during an impact.

As shown in FIG. 5A, an exemplary head model 20 is a cross-sectional bottom head model, or a head model of a bottom portion of a head. This head model has a viewing plane through a translucent cover 34 that is oriented in a generally horizontal plane along the top of the head model. The cross-sectional head model is along a horizontal plane, allowing viewing and measuring of components of the head model in a top-down manner. A fluid component 28 completely surrounds the brain component 26 in this head model. The fluid component 28 is between the brain component 26 and the translucent cover 34 and again, may be translucent to enable image capture of the brain component.

As shown in FIG. 5B, an exemplary head model 20 is a full head model having a translucent head portion 25. The full head model simulates an entire human head and is not cross-section, as was show in FIGS. 4 and 5A. A full head model may allow for more realistic simulations including simulations with a full helmet configured thereon. This translucent head portion may be glass or a clear polymer, such as acrylic, urethane or silicone. A translucent head portion may be made out a single material or a plurality of materials configured to simulate the physical properties or mechanical properties of the human anatomy. The translucent head portion enables viewing of the brain component 26, fluid component 28 and skull component 24 therethrough. In addition, a grid pattern or other marking pattern may be configured on the top surface or plane of the brain component to enable image capture of the grid or pattern. The brain component, fluid component and skull component are all shown in broken lines as they are within the head model.

As shown in FIG. 5C, as shown in FIG. 5B is configured with a full helmet thereon. The helmet 14 has a translucent helmet portion 45 that enables image capture through the translucent helmet portion. A translucent helmet portion may be made out of any suitable material, such as acrylic, polypropylene, polyethylene and the like. In an exemplary embodiment, the translucent helmet portion is made out of a material that substantially simulates the physical and mechanical properties of an actual helmet. As shown in FIG. 5C, a helmet impact element 35 is hitting the head model 20 from the side. The head model 20 has deflected from the impact and the camera 36 is configured to take high speed images or video of the brain component through the translucent helmet 45 component and the translucent head component 25.

As shown in FIG. 6, an exemplary head impact simulator 12 comprises a head model 20 having a skull component 24, brain component 26, fluid component 28, head exterior component 22, dura component 23 and an impact element 38 configured to strike the head model. A camera 36 is configured to take a plurality of images or digital photographs before, during and after the impact element strikes the head model. A high speed camera may be used to provide still images for later analysis. A transparent cover 34 is configured over the head model 20 to enable the camera to take images of the various head model components during an impact simulation. A computer 90 may be employed for analysis of the images and a computer program 92 may be accessed by a microprocessor 96 to provide force, acceleration, and predicted brain trauma resulting from an impact to the head model. Image analysis software 97 may identify various elements within a digital image, such as the brain component perimeter and compare this element from one image to another to determine speed, acceleration, declaration, displacement, and/or deformation of the brain component. As shown in FIG. 6, a digital image 98 of the head model is shown on the display 94. In addition, any number of sensors 88 may be configured on the head model or helmet component including, but not limited to, an accelerometer, stress-strain sensors, etc.

The impact element 38 may be coupled with an actuator 39 having a positioning, speed, acceleration and stroke controls. The head impact simulator may be controlled by a single computer or a plurality of computer. The head model 20 in this embodiment is coupled to a mount 32 by a neck spring 30. The neck spring may simulate a resistance to movement of the head that is representative of a person's neck. A neck spring may be changed in length Lns, or spring constant to model different scenarios. A neck spring may be flexible to allow for some deflection of the head model as a result of an impact. In another embodiment, a neck spring is elastomeric and deflects as a function of an impact and then springs back. An impact element may be configured to hit the head model and then quickly retract to allow the head model to spring back.

As shown in FIG. 7A, an exemplary head model 20 comprises a brain component within the interior cavity 29 of the skull component 24. The brain component is at least partially surrounded by a fluid component 28 used to simulate cerebrospinal fluid. The various components of the head model may be made out of material to simulate the anatomy, having similar density, size, elasticity and the like, or may comprise real components, such as a real brain and/or skull. The head model comprises an exterior component 22 configured to simulate skin and dermal tissue, and a face component 21. As shown in FIG. 7A a distance 80 between the brain component and the skull component 24 may be measured through image analysis. As shown in FIG. 7B, the distance 80 has increased due to an impact by the impact element on the front of the head model, or face portion. The displacement 81 of the brain is the difference between distance 80 in FIG. 7B to the distance 80 in FIG. 7A. The brain component 26 has shifted forward within the interior cavity 29. The front portion of the brain component has deformed to create a deformed portion 82 resulting from the deceleration of the brain component as it is forced forward against the interior wall of the skull component 24. The acceleration of the brain component, as well as the deformation, may be captured and determined by image analysis. A high speed camera may capture a plurality of images that are analyzed by a computer program to determine force, acceleration, deformation and predict brain trauma resulting from an impact. The perimeter of the brain component may be recognized by image analysis software and changes in surface area, displacement and the like may be calculated by analysis of digital images.

As shown in FIG. 8, an exemplary head model 20 has a brain component 26 having a pattern 84 thereon. The pattern shown is a grid pattern, however any suitable pattern including a series of lines configured in one or more directions may be used. In one embodiment, a pattern comprises one or more circles of ovals. The dura component 23, or lining around the perimeter 27 of the brain component in the image side 87 plane, may be a specific thickness and color that facilitates image analysis. The overall volume or surface area of the brain component 26 may be determined by identification of the dura component by image analysis software and computation of the volume therefrom. A dura component may be transparent when configured along the imaging side of the head model. Likewise, imaging analysis software may be configured to identify the grid pattern including the line elements, the intersection points of the line elements or one or more cells of the grid; in this case they are square but may be deformed during testing.

As shown in FIG. 9, an exemplary head model 20 has a brain component 26 with distinct brain portions. The brain portions include the frontal lobe 70, parietal lobe 72, occipital lobe 74, cerebellum 76 and temporal lobe 78. These different brain portions may be identified by image analysis software as an outline pattern and different colors on the brain component 26, as shown. In an exemplary embodiment, the different brain portions may comprise different materials or materials having characteristics to simulate each distinct brain portion.

As shown in FIG. 10, an exemplary head impact simulator 12 has a head model 20, configured with a helmet component thereon, that is being impacted by an impact element 38. The actuator is moving the impact element into contact with the helmet component 14. The helmet component does not have a helmet cover and the impact element is contacting the outer cover 40 of the helmet component. The camera 36 is configured to take photographs or digital images as the impact element strikes the head model 20.

As shown in FIG. 11, an exemplary head impact simulator 12 has a head model 20, configured with a helmet component thereon, that is being impacted by an impact element 38. The actuator is moving the impact element into contact with the helmet component 14. The helmet component has a helmet cover 15 and the impact element is contacting the outer cover outer shell 50 of the helmet cover. Again, the camera 36 is configured to take digital images or digital photographs as the impact element strikes the head model 20. A comparison between the impact test shown in FIG. 10 and the impact test shown in FIG. 11 may provide useful data regarding the effectiveness of helmet covers reducing brain trauma.

As shown in FIG. 12, an exemplary head impact simulator 12 is configured with a head model 20 having a helmet component 14 and a helmet cover 15, thereon. A helmet impact element 35 is configured on an actuator 39 to impact the head model 20. The helmet impact element also has a helmet cover 15' configured thereon. This test may be compared with a similar test, as shown in FIG. 13, without helmet covers on the head model and the helmet impact element, to demonstrate the effectiveness of the helmet cover in reducing brain trauma.

As shown in FIG. 14, an exemplary head impact simulator 12 is configured with a head model 20 having a helmet component 14 and a helmet impact element 35. The helmet impact element is configured to provide an impact to the back portion of the head model. Note that the impact element may be configured to strike the head model in a position and with any direction of motion. A impact element may be configured to move and twist the head model as a result of an impact.

As shown in FIG. 15 an exemplary full head model 20 has a radio-opaque grid 89 configured along a vertical plane within the brain component 26. The radio-opaque grid is comprised of radio-opaque strands 110, such as fibers or metal wires, or a composite of an elastomer or polymer that is filled or coated with a radio-opaque material. The radio-opaque grid may be supple and not restrain movement of the brain component. In addition, a radio-opaque image element 85, a radio-opaque dura 23 will allow for overall area changes of the brain component during an impact test. The radio-opaque grid will further enable determination of motion, compression, elongation, acceleration, velocity and deformation within each grid block or cell. The elastic response of the brain component can be determine through image analysis. An X-ray imaging device 100, is configured in front of the head model 20 to capture images of the radio-opaque image element and grid pattern during a test. Images from an X-ray imaging device may be analyzed by an image analysis software, or the like, to determine a motion factor including displacement, velocity, acceleration, and deformation of the brain component. A radio opaque coating 83 may be configured on or within a head component such on the dura component to enable identification of a head component for image analysis.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A helmet impact test apparatus comprising:
 a) a head model comprising:
  i) a head exterior component
  ii) an interior cavity;
  iii) a skull component;
  iv) a simulated deformable brain component comprising an elastomer having a similar density to a human brain and being elastic, wherein the deformable brain component is configured to elastically deform;
  v) a fluid component;
  vi) an interior cavity surface; and
  vii) a radio-opaque imaging element configured within the head model and comprising:
   radio-opaque strands configured in a radio-opaque grid of intersecting radio-opaque strands configured at offset angles to form discrete cells defined by a perimeter of said radio-opaque strands;
  wherein the head model is coupled with a mount;
  wherein the brain component and fluid component are configured within the interior cavity; and
 b) the mount configured to a least partially restrain the head model;
 c) a helmet component that is configured to fit over the head model;
 d) an impact element configured to impact the helmet component; and
 e) an X-ray imaging device configured to take a plurality of images of the head model when said impact component impacts the helmet;
  wherein the X-ray imaging device is a high speed X-ray imaging system configured to take at least 30 images per second
 f) a computer and a computer program configured to analyze the plurality of images to determine acceleration of the brain component as a function of an impact to the head model by the impact element.

2. The helmet impact test apparatus of claim 1, wherein the radio-opaque imaging element is a coating configured around a portion of the brain component.

3. The helmet impact test apparatus of claim 1, wherein the radio-opaque strands are embedded in the brain component.

4. The helmet impact test apparatus of claim 1, wherein the plurality of radio-opaque strands comprise metal wire.

5. The helmet impact test apparatus of claim 4, wherein the radio-opaque grid is configured in at least one plane of the brain component.

6. The helmet impact test apparatus of claim 5, wherein the radio-opaque grid is configured in two orthogonal planes of the brain component.

7. The helmet impact test apparatus of claim 6, wherein the radio-opaque grid is configured in both a vertical and a horizontal plane of the brain component.

8. The helmet impact test apparatus of claim 7, wherein the radio-opaque grid comprises metal strands.

9. The helmet impact test apparatus of claim 1, further comprising a neck spring component comprising an elastic material that is configured between and coupling together the head model and the mount;
   wherein the neck spring component is flexible thereby causing the head model to recoil after impact from the impact element.

10. The helmet impact test apparatus of claim 1, wherein the brain component is surrounded by the fluid component.

11. The helmet impact test apparatus of claim 10, wherein the radio-opaque imaging element is configured in the fluid component and wherein the fluid component is configured around an outside perimeter of the brain component.

12. The helmet impact test apparatus of claim 1, wherein the impact element is actuated by an actuator that has a velocity control configured to control a velocity of the impact element.

13. The helmet impact test apparatus of claim 1, wherein the impact element is actuated by an actuator that has a stroke control configured to control a length of a stroke of an impact element.

14. The helmet impact test apparatus of claim 1, comprising two or more impact elements configured to impact the helmet component.

15. The helmet impact test apparatus of claim 1, comprising at least one accelerometer sensor attached to the head model.

* * * * *